(12) United States Patent
Nakamura et al.

(10) Patent No.: US 9,074,175 B2
(45) Date of Patent: Jul. 7, 2015

(54) METHOD OF REGENERATING ELASTIC FIBER WITH THE USE OF DANCE OR FACTOR ENHANCING THE EXPRESSION THEREOF

(75) Inventors: Tomoyuki Nakamura, Kyoto (JP); Maretoshi Hirai, Kyoto (JP)

(73) Assignee: NB Health Laboratory Co., Ltd., Sapporo (JP)

( * ) Notice: Subject to any disclaimer, the term of this patent is extended or adjusted under 35 U.S.C. 154(b) by 643 days.

(21) Appl. No.: 11/815,690

(22) PCT Filed: Jan. 23, 2006

(86) PCT No.: PCT/JP2006/301372
§ 371 (c)(1),
(2), (4) Date: Sep. 13, 2007

(87) PCT Pub. No.: WO2006/082763
PCT Pub. Date: Aug. 10, 2006

(65) Prior Publication Data
US 2009/0012273 A1    Jan. 8, 2009

(30) Foreign Application Priority Data

Feb. 7, 2005    (JP) .................................. 2005-030864

(51) Int. Cl.
| | | |
|---|---|---|
| *C12N 5/07* | (2010.01) | |
| *C12N 5/00* | (2006.01) | |
| *A61L 27/50* | (2006.01) | |
| *A61L 27/60* | (2006.01) | |
| *C07K 14/78* | (2006.01) | |

(52) U.S. Cl.
CPC ............ *C12N 5/0031* (2013.01); *A61L 27/507* (2013.01); *A61L 27/60* (2013.01); *C07K 14/78* (2013.01); *C12N 2501/15* (2013.01); *C12N 2501/58* (2013.01); *C12N 2501/998* (2013.01)

(58) Field of Classification Search
None
See application file for complete search history.

(56) References Cited

U.S. PATENT DOCUMENTS

| 6,617,161 B2 * | 9/2003 | Luyten et al. ................. 435/375 |
| 2002/0052044 A1 | 5/2002 | Jeschke et al. |
| 2004/0250303 A1 | 12/2004 | Melchner et al. |
| 2005/0019910 A1 | 1/2005 | Takagi et al. |
| 2007/0218003 A1 | 9/2007 | Nakamura et al. |
| 2012/0196282 A1 | 8/2012 | Nakamura et al. |

FOREIGN PATENT DOCUMENTS

| EP | 1 762 610 A1 | 3/2007 |
| JP | 2002-078484 A | 3/2002 |
| JP | 2003-052360 A | 2/2003 |
| JP | 2003-235548 A | 8/2003 |
| WO | WO 2005/093057 A1 | 10/2005 |

OTHER PUBLICATIONS

Yang et al., "Extracellular Matrix Metalloproteinase 2 Levels Are Regulated by the Low Density Lipoprotein-related Scavenger Receptor and Thrombospondin 2", J. Biol. Chem. 276:8403-8408, 2001.*
Sasaki et al., "Expression of fibulin-2 by fibroblasts and deposition with fibronectin into a fibrillar matrix", J. Cell Sci. 109:2895-2904, 1996.*
GenBank Accession No. NP_006320 (Oct. 2004), 3 pages.*
Ford et al., Prot. Express. Purif. 2:95-107, 1991.*
Dictionary definition of "presence", obtained from encarta.msn.com, last viewed on Aug. 2, 2010, 1 page.*
Bunda, S., "A Search for the Mechanisms by which Various Iron levels Modulate Elastin Production", Thesis, University of Toronto, 2004.*
Katsuta et al., Exp. Dermatol. 17:837-842, 2008.*
Hirai et al., *The Journal of Cell Biology*, 176(7): 1061-1071 (Mar. 26, 2007).
Kuang et al., *Am. J. Physiol. Lung Cell Mol. Physiol.*, 285: L1147-L1152 (2003).
Liu et al., *Nature Genetics*, 36(2): 178-182 (Feb. 2004).
Midwood et al., *Current Biology*, 12(8): R279-R281 (Apr. 16, 2002).
Schiemann et al., *The Journal of Biological Chemistry*, 277(30): 27367-27377 (Jul. 26, 2002).
Tsuruga et al., *The International Journal of Biochemistry & Cell Biology*, 36: 395-400 (2004).
Chong et al., *Amer. J. Pathology*, 166(1): 241-251 (2005).
Giltay et al., *Matrix Biology*, 18: 469-480 (1999).
Hautamaki et al., *Science*, 277: 2002-2004 (1997).
Long et al., *Matrix Biology*, 22: 339-350 (2003).
Nakamura et al., *Nature*, 415: 171-175 (2002).
Nakamura et al., *J. Biological Chem.*, 274(32): 22476-22483 (1999).
Robb et al., *Mol. Biol. of the Cell*, 10: 3595-3605 (1999).
Shapiro et al., *Amer. J. Pathology*, 163(6): 2329-2335 (2003).
Stone et al., *N. Engl. J. Med.*, 351: 346-353 (2004).
Yanagisawa et al., *Nature*, 415: 168-171 (2002).
Nakamura et al., *Jikken Igaku* (*Exp. Medicine*), 20(4): 568-571 (2002).

(Continued)

*Primary Examiner* — David J Steadman
(74) *Attorney, Agent, or Firm* — Leydig, Voit & Mayer, Ltd.

(57) ABSTRACT

The present invention provides a technique for conveniently and efficiently regenerating elastic fiber retaining a normal structure, and a technique enabling preparation of an artificial tissue comprising elastic fiber (for example, artificial skin, artificial blood vessels) that can be transplanted to humans. Specifically, the invention provides a method of producing elastic fiber, comprising culturing (for example, culturing in serum-free medium) cells having the capability of regenerating elastic fiber in the presence of DANCE and/or fibulin-4; artificial elastic fiber comprising DANCE and/or fibulin-4; an elastic fiber regenerating agent; a serum-free medium comprising DANCE and/or fibulin-4; and cells having the capability of regenerating elastic fiber, transfected with at least one of a DANCE expression vector, a fibulin-4 expression vector and a DANCE inducing factor expression vector, and the like.

8 Claims, No Drawings

(56) References Cited

OTHER PUBLICATIONS

Yajima et al., *Nihon Shishuubyo Gakkai Kaishi*, 46(3): 175-184 (2004).
European Patent Office, Extended European Search Report in European Patent Application No. 06712536.9 (Jul. 10, 2009).
International Bureau of WIPO, International Preliminary Report on Patentability in International Patent Application No. PCT/JP2006/301372 (Aug. 7, 2007).
Japanese Patent Office, International Search Report in International Patent Application No. PCT/JP2006/301372 (Mar. 20, 2006).
Japanese Patent Office, Notice of Reasons for Refusal in Japanese Patent Application No. 2007-501548 (May 8, 2012).
Alberts et al., "The Extracellular Matrix of Animal Connective Tissues" in *Molecular Biology of the Cell* (5$^{th}$ edition, pp. 1178-1195), New York, NY: Garland Science, Taylor & Francis Group, LLC (2008).
Hirai et al., *J. Cell Biol.*, 176(7): 1061-1071 (2007).
Kielty et al., *J. Cell Science*, 115(14): 2817-2828 (2002).
McLaughlin et al., *Mol. Cell. Biol.*, 26(5): 1700-1709 (2006).
Mecham, *Methods Enzymol.*, 144: 232-246 (1987).
Dabovic et al., *Journal of Cellular Physiology*, 219: 14-22 (2009).
Noda et al., "The essential role for LTBP-4 in elastic fiber assembly," Poster Presentation No. 2P-0268 at Biochemistry and Molecular Biology BMB 2010, (Dec. 8, 2010).
R&D Systems, Inc., DuoSet ELISA Development Kit Package Insert, Human TGF-β1 Catalog Number: DY240, pp. 1-8 (Apr. 2012).
Son et al., *Journal of Investigative Dermatology*, 124: 1149-1161 (2005).
Sterner-Kock et al., *Genes & Development*, 16: 2264-2273 (2002).
Nonaka et al., *Clinical Biochemistry*, 42: 713-721 (2009).
Saharinen et al., *J. Biol. Chem.*, 273(29): 18459-18469 (1998).
Vliet et al., *Progress in Biophysics & Molecular Biology*, 83: 1-45 (2003).
Japanese Patent Office, Office Action in Japanese Patent Application No. 2009-173172 (Nov. 19, 2013).
Japanese Patent Office, Office Action in Japanese Patent Application No. 2009-173172 (Jun. 24, 2014).

\* cited by examiner

METHOD OF REGENERATING ELASTIC FIBER WITH THE USE OF DANCE OR FACTOR ENHANCING THE EXPRESSION THEREOF

TECHNICAL FIELD

INCORPORATION-BY-REFERENCE OF MATERIAL ELECTRONICALLY SUBMITTED

Incorporated by reference in its entirety herein is a computer-readable nucleotide/amino acid sequence listing submitted concurrently herewith and identified as follows: 4,214 bytes ASCII (Text) file named "701795SequenceListing. txt," created Sep. 13, 2007.

The present invention relates to a novel method of producing elastic fiber, and elastic fiber that can be obtained by the method, and the like.

BACKGROUND ART

With aging, elastic fiber deteriorates and is degraded, leading to the loss of elasticity of the tissues in the body. This does not simply pose problems with body stiffening or skin loosening. Pulmonary emphysema, arterial intimal sclerosis, and aortic aneurysm, which are major diseases in the elderly, and more recently, age related macular degeneration and the like, have been considered to be directly caused by elastic fiber deterioration and decomposition [Hautamaki, R. D. et al. (1997) Science 277(5334): 2002-4; Shapiro, S. D. et al. (2003) American journal of pathology 163(6): 2329-35; Stone, E. M. et al. (2004) The new England journal of medicine 351(4): 346-53; Chong, N. H. et al. (2005) American journal of pathology 166(1): 241-51]. However, the turnover of elastic fiber is very slow; if elastic fiber deteriorates and is degraded, the elastic fiber is not regenerated. Although the elucidation of the mechanisms for formation of elastic fiber is essential for research into the regeneration of elastic fiber, little is known about the molecular mechanisms for elastic fiber formation.

A major reason for the tardy progress of research into elastic fiber formation had been the lack of a good in vitro elastic fiber formation system. Conventionally, to form elastic fiber using cultured cells, not less than 10% fetal bovine serum had been required. For this reason, what in the serum is required for elastic fiber formation remained unknown. For example, it has been reported that in two-dimensional culture of a ciliary body pigment cell line that does not express elastin, elastic fiber is formed by elastin transfection [Robb, B. W. et al. (1999) Molecular biology of the cell 10(11): 3595-605]. However, that approach also uses 10% fetal bovine serum for the cultivation; the roles of factors other than elastin in elastic fiber formation remain unknown.

Use of fetal bovine serum in drugs intended to be transplanted to humans, such as cultured artificial skins and cultured artificial blood vessels, is under strict regulation; it is extremely difficult to prepare an artificial skin or artificial blood vessel containing a normal amount of elastic fiber. It has been reported that elastic fiber was formed in three-dimensional culture of smooth muscle cells or fibroblasts seeded to collagen gel or fibrin gel, and that elastic fiber formation was enhanced by using TGFβ1 and insulin in combination [Long, J. L. et al. (2003) Matrix biology 22(4): 339-50]. However, in this cultivation, because an ingredient derived from a heterologous animal, called 10% fetal bovine serum, is used in all cases, there are many problems with regard to transplantation to humans, and what is required for elastic fiber formation remains unknown. Additionally, the resulting elastic fiber is variegated and cannot be said to have a normal structure.

Therefore, to establish a cell culture technique enabling induction of elastic fiber formation even in the absence of serum is not only extremely important to the elucidation of the molecular mechanisms for elastic fiber formation, but also is in a strong demand for the development of a pharmaceutical that controls elastic fiber formation, and the development of cultured artificial skins or cultured artificial blood vessels comprising elastic fiber retaining a normal structure, and the like.

DISCLOSURE OF THE INVENTION

Therefore, it is an object of the present invention to establish a cell culture technique that enables convenient and efficient formation or regeneration of elastic fiber retaining a normal structure, and formation or regeneration of elastic fiber in serum-free medium, and thereby to provide a means that enables the development of a pharmaceutical that controls elastic fiber regeneration, and a cultured artificial skin or cultured artificial blood vessel comprising elastic fiber retaining a normal structure, and the like.

The present inventors conducted diligent investigations with the aim of solving the above-described problems, and found that in serum-free culture of cells having the capability of forming elastic fiber, by adding a secretory protein known as DANCE (developmental arteries and neural crest epidermal growth factor (EGF)-like; also called fibulin-5) and/or fibulin-4, elastic fiber could be efficiently reproduced. The present inventors also found that TGFβ, known to be capable of inducing the expression of DANCE in fibroblasts [Schiemann et al., J Biol Chem 277 (30): 27367-77 (2002)], had the same activity. DANCE is a secretory protein cloned from cardiovascular tissues in the developmental stage by the present inventors [Nakamura et al., J Biol Chem 274 (32): 22476-83 (1999)]; because DANCE gene deficient mice also prepared and analyzed by the present inventors experienced elastic fiber formation abnormalities, it has been proven that DANCE is essential for elastic fiber formation [Nakamura et al., Nature 415: 171-5 (2002)]. This discovery by the present inventors shows that DANCE is not only essential for elastic fiber formation, but also can be used to regenerate elastic fiber.

This elastic fiber regeneration technique with DANCE and/or fibulin-4, or a DANCE expression inducing factor is not only immediately applicable to the preparation of an artificial skin, skin model or artificial blood vessel comprising elastic fiber retaining a normal amount and a normal structure, but also is considered to be essential for elastic fiber regeneration in vivo.

The present inventors developed the present invention based on these findings. Accordingly, the present invention provides:

[1] A method of producing elastic fiber, comprising culturing a cell having the capability of regenerating elastic fiber in the presence of DANCE;

[2] the method according to [1] above, wherein the cultivation is performed in serum-free medium;

[3] the method according to [1] above, using a medium supplemented with DANCE and/or a DANCE inducing factor, or a cell having the capability of regenerating elastic fiber, incorporating a DANCE expression vector and/or a DANCE inducing factor expression vector;

[4] the method according to [1] above, wherein the DANCE inducing factor is TGFβ;

[5] the method according to [1] above, wherein the DANCE and the cell having the capability of regenerating elastic fiber are derived from a human;

[6] the method according to [1] above, wherein the cell having the capability of reproducing elastic fiber is a fibroblast;

[7] an artificial elastic fiber comprising DANCE, and not comprising an ingredient derived from an animal heterologous to the animal from which the DANCE is derived;

[8] an elastic fiber regenerating agent comprising DANCE or a substance that promotes the expression of DANCE;

[9] a serum-free medium comprising DANCE;

[10] a cell having the capability of regenerating elastic fiber, incorporating at least one of an DANCE expression vector and a DANCE inducing factor expression vector;

[11] a method of producing elastic fiber, comprising culturing a cell having the capability of regenerating elastic fiber in the presence of fibulin-4;

[12] the method according to [11] above, wherein the cultivation is performed in serum-free medium;

[13] an artificial elastic fiber comprising fibulin-4, and not comprising an ingredient derived from an animal heterologous to the animal from which the fibulin-4 is derived;

[14] an elastic fiber regenerating agent comprising fibulin-4 or a substance that promotes the expression of fibulin-4;

[15] a serum-free medium comprising fibulin-4;

[16] a cell having the capability of regenerating elastic fiber, incorporating a fibulin-4 expression vector.

BEST MODE FOR EMBODYING THE INVENTION

The present invention provides a method of producing elastic fiber, comprising culturing a cell having the capability of regenerating elastic fiber in the presence of DANCE and/or fibulin-4.

"DANCE" (also called fibulin-5) refers to a human DANCE (see, for example, GenBank accession number: AF112152) or an ortholog thereof, or a mutant thereof (including SNP and haplotype). The ortholog of DANCE is not subject to limitation, and can be derived from, for example, an optionally chosen animal, preferably a mammal. As examples of the mammal, cattle, sheep, swine, sheep, monkey, rabbit, rat, hamster, guinea pig, mouse and the like can be mentioned. DANCE is a secretory protein, and can be deprived of a signal sequence (for example, corresponding to the 1st to 23rd amino acid residues in the amino acid sequence shown by SEQ ID NO:1) by processing. In the method of the present invention, as DANCE, any of one deprived of the signal sequence and one not deprived of the signal sequence can be used, but one deprived of the signal sequence is preferable. DANCE has also been confirmed to undergo cleavage by DANCE-specific protease. For example, referring to the amino acid sequence shown by SEQ ID NO:1, Arg-Gly (corresponding to the 77th to 78th amino acids in the amino acid sequence shown by SEQ ID NO:1) can be cleaved. Because cleaved form DANCE has been confirmed to be weak in the capability of regenerating elastic fiber, the DANCE used in the present invention is preferably a full-length form DANCE (i.e., one not cleaved as described above).

The DANCE mutant is not subject to limitation, as long as it enables elastic fiber regeneration, and is, for example, an amino acid sequence having 1 or 2 or more (for example, 1 to 30, preferably 1 to 20, more preferably 1 to 10, most preferably 1 to 5) amino acids substituted, deleted, inserted or added in the amino acid sequence shown by SEQ ID NO:1. As the DANCE mutant, one having a mutation introduced to the protease cleavage site so that it exhibits resistance to DANCE-specific protease can be used. For example, one having the protease cleavage site (Arg-Gly: corresponding to the 77th to 78th amino acids in the amino acid sequence shown by SEQ ID NO:1) or amino acids in the vicinity thereof (for example, the 70th to 85th, preferably 72nd to 83rd, more preferably 74th to 81st, still more preferably 76th to 79th amino acids in the amino acid sequence shown by SEQ ID NO:1) mutated (for example, deleted, added, substituted) so that it exhibits resistance to DANCE-specific protease in the amino acid sequence shown by SEQ ID NO:1 can be used. "Exhibits resistance to DANCE-specific protease" means that the DANCE cleavage capability of DANCE-specific protease further decreases after the mutation (for example, a reduction of 1.5 times or more, preferably 2 times or more), and the degree of reduction in the cleavage capability is not subject to limitation. Whether or not the DANCE mutant exhibits resistance to DANCE-specific protease can be determined by measuring and comparing the amounts of normal DANCE and DANCE mutant cleaved after a cleavage treatment of normal DANCE and the DANCE mutant (see, for example, Reference Example below). As such, the DANCE mutant is considered to have a longer half-life than that of natural form DANCE, and is therefore useful in the method of the present invention.

Fibulin-4 refers to human fibulin-4 (see, for example, GenBank accession number: NM_021474) or an ortholog thereof, or a mutant thereof (including SNP and haplotype). The ortholog of fibulin-4 is not subject to limitation, and can be, for example, one derived from the above-described animal. Fibulin-4 is a secretory protein, and can be deprived of a signal sequence thereof removed by processing. In the method of the present invention, any of one deprived of the signal sequence and one not deprived of the signal sequence can be used as fibulin-4, but one deprived of the signal sequence is preferable. The fibulin-4 mutant is not subject to limitation, as long as it enables regeneration of elastic fiber, and is, for example, an amino acid sequence having 1 or 2 or more (for example, 1 to 30, preferably 1 to 20, more preferably 1 to 10, most preferably 1 to 5) amino acids substituted, deleted, inserted or added in the amino acid sequence that encodes fibulin-4.

"A cell having the capability of regenerating elastic fiber" refers to a cell that secretes elastic fiber constituents, and that enables the neogenesis of elastic fiber by being cultured in the presence of DANCE and/or fibulin-4. The cell having the capability of regenerating elastic fiber can be one derived from an optionally chosen animal, preferably a mammal. As the mammal, the same as that from which the ortholog of DANCE and/or fibulin-4 is derived can be mentioned. The cell having the capability of regenerating elastic fiber can also be a non-transfected cell or a transfected cell.

When the cell having the capability of regenerating elastic fiber is a non-transfected cell, the cell can be a cell derived from a tissue wherein elastic fiber is present, for example, the skin, blood vessels (e.g., artery), lung or uterus. The cell can also be a fibroblast, a smooth muscle cell, an epithelial cell, or an endothelial cell and the like.

Preferably, as the cell, a skin fibroblast or a vascular smooth muscle cell can be used. The cell having the capability of regenerating elastic fiber can further be a primary cultured cell, a cell line derivatized from a primary cultured cell, or a cell obtained by culturing an undifferentiated cell such as a stem cell. Such a cell can be prepared by a method known per se (see, for example, Current Protocols in Cell Biology, John Wiley & Sons, Inc. (2001); Kino Saibou no Bunri to Baiyo, Maruzen Shoten (1987)).

When the cell having the capability of regenerating elastic fiber is a transfected cell, the cell can be one transfected with 1 or 2 or more genes in a way allowing the expression thereof. When the cell to be transfected is a cell lacking or not sufficiently having the capability of regenerating elastic fiber, a cell having acquired the capability of regenerating elastic fiber, or a cell having the improved capability of regenerating elastic fiber can be prepared by introducing a vector capable of expressing elastic fiber constituents and/or another factor that promotes the formation of elastic fiber to the cell. Of course, a vector capable of expressing elastic fiber constituents and/or another factor that promotes the formation of elastic fiber may be introduced to the aforementioned cell such as a skin fibroblast or a vascular smooth muscle cell to further improve its capability of regenerating elastic fiber. Because DANCE is considered to organize elastic fiber constituents (in detail, DANCE, with microfibril as the scaffold, localizes an enzyme of the lysyloxidase family (an enzyme that crosslinks elastin) on the microfibril to thereby allow elastin deposition and crosslinking to occur on the microfibril), and also because fibulin-4 is also considered to be capable of playing an important role in elastic fiber formation, by transfecting a cell lacking or not sufficiently having the capability of regenerating elastic fiber with such a vector, the cell transfected is considered to become capable of secreting the necessary elastic fiber constituents, and to become capable of newly generating elastic fiber by being cultured in the presence of DANCE and/or fibulin-4. The elastic fiber constituents and/or other factor that promotes the formation of elastic fiber to be expressed in a cell lacking or not sufficiently having the capability of regenerating elastic fiber is not subject to limitation, and can be determined as appropriate by those skilled in the art according to the kind of cell; for example, as the elastic fiber constituents, elastin, lysyloxidase (LOX), lysyloxidase-like 1-4 (LOXL1-4), LTBP 2 and 4, fibrillin 1-3, EMILIN 1 and 2, MAGP 1 and 2 and the like can be mentioned; as the other factor that promotes the formation of elastic fiber, versican V3, hyaluronidase and the like can be mentioned. As the vector capable of expressing elastic fiber constituents and/or another factor that promotes the formation of elastic fiber and the method of introducing the vector to a cell, the same as the DANCE expression vector and/or fibulin-4 expression vector, and DANCE inducing factor expression vector described below can be used.

Cultivation of a cell having the capability of regenerating elastic fiber in the presence of DANCE and/or fibulin-4 is not subject to limitation, as long as it results in cultivation of the cell having the capability of regenerating elastic fiber in a culture medium containing DANCE and/or fibulin-4. Therefore, at the start of cultivation, the DANCE and/or fibulin-4 protein may not be present in the medium. As examples of cultivation of a cell having the capability of regenerating elastic fiber in the presence of DANCE and/or fibulin-4, (1) cultivation of a cell having the capability of regenerating elastic fiber in a culture medium supplemented with DANCE and/or fibulin-4, (2) cultivation of a cell having the capability of regenerating elastic fiber in a culture medium supplemented with a DANCE induction factor, (3) cultivation of a cell having the capability of regenerating elastic fiber, transfected with a DANCE expression vector and/or a fibulin-4 expression vector, and/or a DANCE inducing factor expression vector, (4) co-cultivation of a cell having the capability of regenerating elastic fiber with a DANCE expressing cell and/or a fibulin-4 expressing cell, and/or a DANCE inducing factor expressing cell and the like can be mentioned. In the method of the present invention, the density of the cell having the capability of regenerating elastic fiber at the time it is seeded to the culture medium is not subject to limitation; for example, it can be seeded so that it becomes subconfluent or confluent.

In the case (1) above, the DANCE and/or fibulin-4 added to the culture medium can be a natural protein or a recombinant protein. DANCE and fibulin-4 can be prepared by a method known per se; for example, a) DANCE or fibulin-4 may be recovered from a biological sample (for example, blood) containing DANCE or fibulin-4, b) by introducing a DANCE expression vector or a fibulin-4 expression vector (described below) to a host cell (for example, bacterium of the genus *Escherichia*, bacterium of the genus *Bacillus*, yeast, insect cell, insect, animal cell) to prepare a transformant, and the DANCE or fibulin-4 produced by the transformant may be recovered, c) DANCE or fibulin-4 may be synthesized using a cell-free system using rabbit reticulocyte lysate, wheat germ lysate, *Escherichia coli* lysate and the like. DANCE and fibulin-4 are purified as appropriate by methods based on solubility, such as salting-out and solvent precipitation; methods based mainly on differences in molecular weight, such as dialysis, ultrafiltration, gel filtration, and SDS-polyacrylamide gel electrophoresis; methods based on differences in electric charge, such as ion exchange chromatography; methods based on specific affinity, such as affinity chromatography and use of DANCE antibody; methods based on differences in hydrophobicity, such as reverse phase high performance liquid chromatography; methods based on differences in isoelectric point, such as isoelectric focusing; combinations thereof, and the like. The amounts of DANCE and fibulin-4 added to the culture medium are not subject to limitation, as long as they enable regeneration of elastic fiber; for example, an amount such that the final concentration in the culture medium will be 0.1 to 100 µg/ml, preferably 0.5 to 50 µg/ml, more preferably 1 to 20 µg/ml, can be added.

In the case (2) above, the DANCE inducing factor added to the culture medium is not subject to limitation, as long as it is capable of inducing the expression of DANCE; for example, TGFβ (for example, TGFβ1) and the like can be mentioned. When the DANCE inducing factor is a protein, a natural protein or a recombinant protein (can be prepared in the same manner as with DANCE) can be used. The amount of DANCE inducing factor added to the culture medium is not subject to limitation, as long as it induces DANCE in an amount that enables regeneration of elastic fiber; for example, when TGFβ is used as the DANCE inducing factor, an amount such that the final concentration in the culture medium will be 0.5 to 1000 ng/ml, preferably 1 to 100 ng/ml, more preferably 5 to 40 ng/ml, can be added.

In the case (3) above, the expression vector introduced to the cell having the capability of regenerating elastic fiber can be the above-described vector capable of expressing DANCE or fibulin-4 or a DANCE inducing factor. These expression vectors must have the polynucleotide that encodes the desired protein functionally linked to a promoter capable of exhibiting promoter activity in the target cell. The promoter used is not subject to limitation, as long as it is capable of functioning in the target cell; for example, virus promoters such as the SV40-derived early promoter, cytomegalovirus LTR, Rous sarcoma virus LTR, MoMuLV-derived LTR, and adenovirus-derived early promoter; and mammalian constituent protein gene promoters such as the β-actin gene promoter, PGK gene promoter, and transferrin gene promoter, and the like can be mentioned. The promoter may also be a promoter specific for a cell having the capability of regenerating elastic fiber, such as a fibroblast-specific promoter (for example, collagen promoter) or a smooth muscle cell-specific promoter (for example, SM22 promoter, α-smooth muscle actin promoter).

The expression vector preferably comprises a transcription termination signal, that is, a terminator region, downstream of the polynucleotide that encodes the desired protein. Furthermore, the expression vector may further comprise a selection marker gene for selection of transformant cells (a gene that confers resistance to a drug such as tetracycline, ampicillin, kanamycin, hygromycin, or phosphinothricin, a gene that compensates for an auxotrophic mutation, and the like). The backbone vector used as the expression vector is not subject to limitation; for example, plasmid vectors, and viral vectors such as retrovirus, adenovirus, adeno-associated virus, and Sendai virus can be mentioned.

Introduction of the expression vector to a cell having the capability of forming elastic fiber can be performed by a method known per se, for example, electroporation, calcium phosphate precipitation, microinjection, a method using a lipid such as liposome or cationic lipid and the like. A portion or whole of the expression vector may be incorporated, or may not be incorporated, in the genome of the cell having the capability of forming elastic fiber. For incorporation of the expression vector into the intracellular genome, a method known per se, for example, a method using retrovirus, a method using a targeting vector enabling homologous recombination and the like can be used.

In the case (4) above, the cell to be co-present with the cell having the capability of forming elastic fiber in the culture medium is not subject to limitation, as long as it is capable of expressing DANCE or fibulin-4, or a DANCE inducing factor. The expressing cell can be, for example, a cell obtained by introducing an expression vector of DANCE or of fibulin-4, or of DANCE inducing factor to a host cell, or a natural cell that expresses DANCE or fibulin-4, or a DANCE inducing factor. As the natural cell that expresses DANCE, a cell derived from a DANCE expressing tissue (for example, heart, kidney, pancreas, testis, ovary, small intestine, colon, cartilage, artery, lung, uterus, skin) can be used. As the natural cell that expresses fibulin-4, a cell derived from a fibulin-4 expressing tissue (for example, heart, brain, placenta, lung, liver, skeletal muscle, kidney, pancreas, spleen, prostate, testis, ovary, small intestine, large intestine, skin, artery) can be used. As the natural cell that expresses a DANCE inducing factor, when TGFβ, for example, is intended as the DANCE inducing factor, a cell derived from a tissue such as leukocytes, bone, placenta, spleen, small intestine, colon, liver, kidney, heart, brain, bone marrow, and cartilage can be used. The DANCE or fibulin-4 or DANCE inducing factor expressing cell can also be a primary cultured cell, a cell line derivatized from a primary cultured cell, a cell (for example, differentiated cells) obtained by culturing an undifferentiated cell such as a stem cell, a commercially available cell line, a cell line available from a cell bank and the like. The DANCE expressing cell or fibulin-4 expressing cell, or DANCE inducing factor expressing cell can also be a cell derived from the same animal species as the cell having the capability of regenerating elastic fiber.

Included as the co-cultivation are a case where the cell having the capability of forming elastic fiber and the DANCE expressing cell or fibulin-4 expressing cell, or DANCE inducing factor expressing cell are physically contacted with each other and a case where these cells are present in the same culture system but are mutually isolated by a septum allowing the passage of substances so that they cannot physically contact with each other. As an example of the case where the cell having the capability of forming elastic fiber and the DANCE expressing cell or fibulin-4 expressing cell, or DANCE inducing factor expressing cell are present in the same culture system but are mutually isolated by a septum allowing the passage of substances so that they cannot physically contact with each other, a case where the two kinds of cells are cultured in mutual isolation using a filter (for example, Culture Insert) for ordinary cell culture can be mentioned.

The above-described cultivation of a cell having the capability of regenerating elastic fiber in the presence of DANCE and/or fibulin-4 can be performed in accordance with an ordinary method of cell culture. For example, as the basal medium, MEM, DMEM, RPMI1640 and the like can be used. The basal medium may be supplemented with ingredients such as amino acids, vitamins, lipids, antibiotics, and buffering agents. The pH of the medium is, for example, about 6 to 8, preferably about 6.5 to 7.5. Cultivation temperature is, for example, about 30 to 40° C., preferably about 37° C. Cultivation time can be adjusted as appropriate to obtain a sufficient amount of elastic fiber.

Although the above-described cultivation may be performed in any of a serum-free medium and a serum medium (for example, not more than 5%, not more than 3% or not more than 1% serum contained), it is preferable, from the viewpoint of prevention of contamination with unidentified ingredients, reduction in the infection risk, and the like, that the cultivation be performed in a serum-free medium. Furthermore, from the viewpoint of removal of ingredients derived from heterologous animals (for example, to suppress allergic reactions), it is preferable that the DANCE and/or fibulin-4, and cell having the capability of regenerating elastic fiber, and other ingredients, used for the cultivation share the same derivation from the same animal species.

To allow the cell having the capability of regenerating elastic fiber to more efficiently form elastic fiber, the medium used in the above-described cultivation can also contain elastic fiber constituents other than DANCE and/or fibulin-4 (for example, elastin, lysyloxidase (LOX), lysyloxidase-like 1-4 (LOXL1-4), LTBP 2 and 4, fibrillin 1-3, EMILIN 1 and 2, MAGP 1 and 2), and/or other factors that promote the formation of elastic fiber (for example, versican V3, hyaluronidase), and/or other ingredients (for example, betaig-h3, 67 kD elastin-binding protein).

The cultivation can also be two-dimensional culture or three-dimensional culture. The two-dimensional culture or three-dimensional culture can be performed by a method known per se. For example, for technique concerning three-dimensional culture, see Long, J. L. et al. (2003) Matrix biology 22(4): 339-50, Muraguchi, T. et al., (1994) Plastic and Reconstructive Surgery 93(3): 537-44.

Whether or not elastic fiber was produced (that is, regenerated) can be determined by a method known per se. For example, a portion of the culture is collected and immunostained with an antibody against an elastic fiber constituent, such anti-DANCE antibody, anti-fibulin-4 antibody, and anti-elastin antibody, whereby the determination is achieved.

The present invention also provides artificial elastic fiber comprising DANCE and/or fibulin-4. As used herein, "artificial elastic fiber" is understood to mean elastic fiber regenerated in vitro.

The artificial elastic fiber of the present invention can be one not comprising an ingredient derived from an animal heterologous to the animal from which the DANCE and/or fibulin-4 used for the cultivation, and/or the cell having the capability of regenerating elastic fiber used for the cultivation, is derived. That is, the artificial elastic fiber of the present invention can be one consisting exclusively of an animal-derived biological ingredient derived from a single animal species. The above-described method of the present invention has made it possible to provide such an artificial elastic fiber for the first time. Therefore, the artificial elastic fiber of the present invention can be suitably used in transplantation between same species such as allogeneic transplantation. Also, by using a cell derived from an individual for which transplantation is desired as the cell having the capability of regenerating elastic fiber, and using a medium not contaminated with an ingredient derived from a heterologous animal at all, elastic fiber that can be suitably used for syngeneic transplantation can be obtained.

The artificial elastic fiber of the present invention can also comprise elastic fiber constituents other than DANCE and/or fibulin-4 (for example, elastin, lysyloxidase (LOX), lysyloxidase-like 1-4 (LOXL1-4), LTBP2 and 4, fibrillin 1-3, EMILIN 1 and 2, MAGP 1 and 2), and other ingredients (for example, betaig-h3, 67 kD elastin-binding protein).

The artificial elastic fiber of the present invention can also be provided in a form accompanied by a cell having the capability of regenerating elastic fiber (that is, a complex comprising the artificial elastic fiber of the present invention and a cell having the capability of regenerating elastic fiber). For example, a culture obtained by the method of the present invention corresponds to this form. Of course, the artificial elastic fiber of the present invention can also be provided as a form not accompanied by a cell having the capability of regenerating elastic fiber. This form is obtained by a method known per se. For example, by subjecting a culture obtained by the method of the present invention to a treatment such as a cell removal treatment (for example, EDTA treatment), radiation (for example, γ rays), or a cell denaturation treatment (for example, freeze-thawing, freeze-drying), artificial elastic fiber not accompanied by a cell having the capability of regenerating elastic fiber can be obtained.

The present invention further provides an artificial tissue comprising the above-described elastic fiber. As examples of the artificial tissue comprising the elastic fiber, artificial skins, artificial blood vessels (for example, artificial artery), artificial lung, artificial uterus and the like can be mentioned, and artificial skins and artificial blood vessel are preferable. The artificial tissue of the present invention can be prepared by a method known per se (see, for example, Long, J. L. et al. (2003) Matrix biology 22(4): 339-50, Muraguchi, T. et al., (1994) Plastic and Reconstructive Surgery 93(3): 537-44).

The present invention also provides an elastic fiber regenerating agent comprising DANCE and/or fibulin-4 (protein) or a substance that promotes the expression of DANCE and/or fibulin-4.

The substance that promotes the expression of DANCE is not subject to limitation, as long as it enables the expression of DANCE; for example, a DANCE expression vector, a DANCE inducing factor, and a DANCE inducing factor expression vector can be mentioned.

The substance that promotes the expression of fibulin-4 is not subject to limitation, as long as it enables the expression of fibulin-4; for example, a fibulin-4 expression vector can be mentioned.

The regenerating agent of the present invention, when formulated with an optionally chosen carrier, for example, a pharmaceutically acceptable carrier, is useful for preventing, treating, or ameliorating a condition or disease for which regeneration of elastic fiber is desired, for example, pulmonary emphysema, vascular injury, cutis laxa, wounds, elastic fiber deterioration (for example, those caused by aging or ultraviolet), chapped skin, arteriosclerosis, aortic aneurysm, age related macular degeneration, perineal hernia, and anal hernia, or for cosmetic purposes such as removing skin loosening and wrinkles. The regulating agent of the present invention is also useful as a reagent for culturing a cell having the capability of regenerating elastic fiber.

The pharmaceutically acceptable carrier is exemplified by, but not limited to, excipients such as sucrose, starch, mannit, sorbit, lactose, glucose, cellulose, talc, calcium phosphate, calcium carbonate and the like, binders such as cellulose, methylcellulose, hydroxypropylcellulose, polypropylpyrrolidone, gelatine, gum arabic, polyethylene glycol, sucrose, starch and the like, disintegrating agents such as starch, carboxymethyl cellulose, hydroxypropyl starch, sodium-glycolstarch, sodium hydrogen carbonate, calcium phosphate, calcium citrate and the like, lubricants such as magnesium stearate, aerosil, talc, sodium lauryl sulfate and the like, aromatics such as citric acid, menthol, glycyrrhizin ammonium salt, glycine, orange powder and the like, preservatives such as sodium benzoate, sodium bisulfite, methylparaben, propylparaben and the like, stabilizers such as citric acid, sodium citrate, acetic acid and the like, suspending agents such as methylcellulose, polyvinylpyrrolidone, aluminum stearate and the like, dispersing agents such as surfactant and the like, diluents such as water, physiological saline, orange juice and the like, base wax such as cacao butter, polyethylene glycol, refined kerosene and the like, and the like.

A preparation which is suitable for oral administration is, for example, a liquid comprising an effective amount of a ligand dissolved in a diluent such as water, physiological saline and orange juice, a capsule, sachet or tablet comprising an effective amount of a ligand as a solid or granules, a suspension comprising an effective amount of a ligand in a suitable dispersion medium, an emulsion comprising a solution of an effective amount of a ligand dispersed and emulsified in a suitable dispersion medium and the like.

A preparation preferable for parenteral administration (e.g., intravenous injection, subcutaneous injection, intramuscular injection, topical injection, intraperitoneal administration and the like) includes, for example, an aqueous or non-aqueous isotonic sterile injection which may contain antioxidant, buffer, bacteriostatic agent, isotonicity agent and the like. It may be an aqueous or non-aqueous sterile suspension which may contain suspension, solubilizer, thickener, stabilizer, preservative and the like. The preparation can be sealed in a container in a unit dose or plural doses like an ampoule or vial. It is also possible to lyophilize a ingredient and a pharmaceutically acceptable carrier and preserve them in a state that only requires dissolving or suspending in a suitable sterile vehicle immediately before use.

While the dose of the preparation of the present invention varies depending on the kind and activity of the ingredient, degree of seriousness of the disease, the animal species to be the administration subject, drug acceptability, body weight and age of the administration subject, and the like, it is generally about 0.05-about 100 mg/kg a day for an adult in the amount of the ingredient.

The present invention also provides optionally chosen materials used in the method of the present invention, for example, a serum-free medium, a DANCE expression vector and/or a fibulin-4 expression vector, a cell transfected with a DANCE expression vector and/or a fibulin-4 expression vector, and the like.

The contents of all the references cited herein are hereby incorporated in their entireties by reference, to the extent that they have been disclosed herein.

The present invention is explained in more detail by referring to Examples, which are mere illustration and not to be construed as limitative.

EXAMPLES

1. Materials and Methods

1.1. Materials

Dulbecco's Modified Eagle Medium (DMEM), Dulbecco's Modified Eagle's Medium/Ham's Nutrient Mixture F12 (DMEM/F12), bovine serum albumin (BSA), and the monoclonal anti-FLAG.M2 antibody (F3165) were purchased from Sigma; fetal bovine serum (FBS) was purchased from JRH Bioscience. The anti-mouse DANCE antibody BSYN1923 was prepared by immunizing a rabbit with a synthetic peptide corresponding to the mouse DANCE 76-98 amino acid, and affinity-purified using a column with an antigen peptide immobilized thereon. Anti-Myc (9E10) antibody was purchased from Santa Cruz. Polyclonal anti-elastin antibody (PR533) was purchased from Elastin Products Company, INC. Anti-rabbit Alexa Fluor 488 antibody and anti-mouse Alexa Fluor 546 antibody were purchased from Molecular Probes. Microscope Cover Glass was purchased from Fisherbrand and Vectashield was purchased from Vector Laboratories.

1.2. Recombinant DANCE

Using 293T cells and a DANCE expression vector, a cell line that stably expresses human DANCE was prepared, and recombinant DANCE was purified from the culture supernatant thereof using Ni-NTA agarose (Qiagen), after which it was desalinized using a desalinization column (Amersham).

1.3. Cultivation of Fibroblasts

Human fibroblasts were kindly supplied by the Department of Plastic Surgery, Kyoto University Hospital. A cover glass was placed on the bottom of a 24-well plate, on which human fibroblasts were seeded at $7.5 \times 10^4$ cells per well, and cultured in a DMEM medium supplemented with 10% FBS at 37° C. in the presence of 5% $CO_2$. After the plate was washed with PBS on Day 3, the medium was exchanged with a DMEM/F12 medium not supplemented with FBS, and purified DANCE protein, cleaved form of DANCE protein 4 µg/ml, or FBS was added. Cultivation was continued at 37° C. in the presence of 5% $CO_2$, and the cells were fixed and immunostained on Day 14.

1.4. Immunostaining

On Day 14 of cultivation, the cells were washed with 1 ml of PBS three times, after which they were fixed with 100% methanol at −20° C. for 30 minutes. After washing with PBS, the cells were subjected to blocking with a PBS containing 2% BSA at room temperature for 30 minutes, after which the cells were incubated with the polyclonal anti-elastin antibody (1/100) and the monoclonal anti-FLAG antibody (1/100) at room temperature for at least 1 hour. The cells were washed with PBS and further incubated with the anti-rabbit Alexa Fluor 488 antibody (1/100) and the anti-mouse Alexa Fluor 546 antibody (1/100) at room temperature for 1 hour. After washing with PBS, the cells were fixed with 4% para-formaldehyde at room temperature for 10 minutes and again washed with PBS, after which the sample was mounted onto a glass slide using a DAPI-containing Vectashield. Examination was performed using a confocal laser scan microscope (LSM510, Zeiss).

Reference Example 1

Some DANCE has been Cleaved at N-Terminus In Vitro and In Vivo

1.1. Forced Expression of Human and Mouse Dance in 293T Cells 293T cells were transfected with human and mouse DANCE cDNAs with FLAG tag added immediately downstream of the signal peptide cleavage site; after the medium was exchanged with serum-free medium, cultivation was continued for 48 hours, 15 µl of the culture supernatant was developed by SDS-PAGE, and Western blotting was performed. The antibodies used were BSYN obtained by immunizing a rabbit with a peptide corresponding to mouse the DANCE 76-98th amino acids, and anti-FLAG M2 antibody.

As a result, BSYN did not recognize human DANCE, and mouse DANCE was detected as two bands. In contrast, anti-FLAG M2 antibody detected human and mouse DANCE as a single band.

1.2. Expression of DANCE in Mouse-Derived Skin Fibroblasts

Fibroblasts from skins of neonatal DANCE knockout mice [see Nature 415: 171-175 (2002)] and control mice of the same litter were cultured and labeled with $^{35}$S-Met and Cys for 24 hours, after which the culture supernatant was immunoprecipitated with BSYN antibody. The immunoprecipitate was developed by SDS-PAGE and detected by autoradiography.

As a result, two bands were detected in the skin fibroblasts from the DANCE+/+mice, whereas no bands were detected in the skin fibroblasts from the DANCE−/−mice.

1.3. Western Blot of Mouse Lung Tissue

Lung tissue extracts from 12-week-old DANCE knockout mice and control mice of the same litter were developed by SDS-PAGE and Western blotting was performed with BSYN antibody.

As a result, DANCE was detected as two bands in the lung tissue of the DANCE+/+mice, whereas no bands were detected in the lung tissue of the DANCE−/−mice.

Reference Example 2

N-Terminus of Cleaved form of DANCE Agrees with the 78th and Following Amino Acids of Dance 293T cells were transfected with a human DANCE cDNA with FLAG tag and 6×His tag added to the carboxyl terminus thereof to establish a cell line showing stable expression. The recombinant DANCE was purified from 800 ml of the serum-free culture supernatant using Ni-NTA agarose (Qiagen), developed by SDS-PAGE, and stained with Coomassie-Blue. Of the major two bands, the band corresponding to the cleaved form of DANCE was cut out and analyzed by Edman degradation to determine the N-terminal amino acid sequence thereof.

As a result, the N-terminal amino acid sequence of the cleaved form of DANCE agreed with the amino acid sequence at the 78th and subsequent positions of DANCE.

Hence, it was considered that this low-molecular protein is produced due to the cleavage of DANCE between the 77th amino acid and the 78th amino acid.

Reference Example 3

Cleavage of DANCE is Inhibited by Serine Protease Inhibitor 293T cells were transfected with a human DANCE cDNA with FLAG tag and 6×His tag added to the carboxyl terminus thereof; the cells were cultured using a serum-free medium comprising a cysteine protease inhibitor (E64) or serine protease inhibitor (aprotinin) for 48 hours; a recombinant protein was precipitated from the culture supernatant using Ni-NTA agarose and was developed by SDS-PAGE and Western blotting was performed using anti-FLAG M2 antibody.

As a result, the cleavage of DANCE was not inhibited by E64 but inhibited by aprotinin.

Hence, it was suggested that DANCE is cleaved by serine protease.

Reference Example 4

DANCE Becomes Resistant to Cleavage when Arg77 is Substituted with Ala 293T cells were transfected with an expression vector for the mutated form of DANCE resulting from the substitution of the 77th arginine of DANCE with alanine (with C-terminal FLAG and 6×His tag), and an expression vector for normal form of DANCE (with C-terminal FLAG and 6×His tag); the cells were cultured using serum-free medium for 48 hours; a recombinant protein was precipitated from the culture supernatant using Ni-NTA agarose, and developed by SDS-PAGE, and Western blotting was performed using anti-FLAG M2 antibody.

As a result, this mutated form of DANCE was shown to exhibit resistance to cleavage with a protease.

Example 1

DANCE Protein is Capable of Inducing Elastic Fiber Formation in Serum-Free Culture Human skin fibroblasts were seeded to reach confluency; the medium was replaced with serum-free medium or a medium containing 10% fetal calf serum; the cells were cultured for 2 weeks; the formation of elastic fiber was examined by immunostaining with anti-elastin antibody.

As a result, with the medium containing 10% fetal calf serum, formation of elastic fiber was observed. Although cells survived in the serum-free medium, elastic fiber was hardly formed. However, when recombinant DANCE protein had been added to serum-free medium at 4 μg/ml, elastic fiber was formed at a level equivalent to or above that with the serum-containing medium. When the localization of the recombinant DANCE added at that time was examined using anti-FLAG antibody, it was found to be co-localized with the elastic fiber formed. Even when 10 ng/ml of TGFβ1, which has been reported to induce the expression of DANCE, was added in place of the recombinant DANCE, similar elastic fiber formation was observed.

Example 2

Induction of Elastic Fiber Formation by DANCE does Not Depend on Integrin but Requires Amino-Terminal Domain Next, whether or not induction of elastic fiber formation by DANCE requires its binding to cell surface integrin, and whether or not amino-terminal domain cleavage by protease influences the activity were examined. Recombinant protein was added to obtain a concentration of 4 μl/ml in all cases.

As a result, almost no elastic fiber formation was observed in the cultivation in serum-free medium, whereas a large amount of elastic fiber was formed in the medium supplemented with recombinant DANCE protein. Because equivalent elastic fiber formation was observed even in a medium supplemented with a mutant protein confirmed to minimally bind to integrin (one prepared by mutating the integrin-binding site RGD to RGE), it was considered that in elastic fiber formation, the binding of DANCE and integrin was not necessary. In contrast, in the medium supplemented with amino-terminal domain cleaved form DANCE (AND-DANCE), the formation of elastic fiber was very little; it was considered that cleaved form DANCE has almost no activity to form elastic fiber, or a very weak activity. When the lysyl oxidase inhibitor BAPN (beta-aminopropionitrile) had been added along with full-length DANCE, no elastic fiber was formed because elastin crosslinking was inhibited. However, even at this time, the DANCE protein added was distributed in a fibrous form. Hence, it can be considered that DANCE does not require elastin to be distributed in a fibrous form.

Example 3

Fibulin-4 Protein is Capable of Inducing Elastic Fiber Formation in Serum-Free Culture Next, according to the same method as Example 1, human skin fibroblasts were seeded to achieve a confluent state, the medium was replaced with a serum-free medium or a medium comprising 10% fetal bovine serum, the fibroblasts were cultured for 2 weeks, and elastic fiber formation was examined by immunostaining with anti-elastin antibody.

As a result, elastic fiber formation was observed in the medium comprising 10% fetal bovine serum. Although the cells survived in the serum-free medium, almost no elastic fiber was formed. However, when recombinant fibulin-4 protein had been added to the serum-free medium to obtain a concentration of 4 μg/ml, elastic fiber was formed at a level equivalent to or above that with the serum-containing medium. At this time, the localization of the recombinant fibulin-4 added was examined using an anti-FLAG antibody; the recombinant fibulin-4 was found to be co-localized with the elastic fiber formed.

Discussion

Because it has been recognized to date that 10% fetal bovine serum is essential for forming elastic fiber in in vitro cell culture, the factor required for elastic fiber formation contained in the serum remained unidentified. The present inventor showed that simply by adding DANCE or fibulin-4 or a factor that enhances the expression of the DANCE gene (TGFβ) to the medium, it was possible to allow human skin fibroblasts to efficiently produce elastic fiber. These results suggest that the presence of DANCE or fibulin-4 or a factor that enhances the expression of the DANCE gene (TGFβ) is sufficient to induce elastic fiber formation in human skin fibroblasts.

Industrial Applicability

The method of the present invention is useful for the convenient and efficient regeneration of elastic fiber retaining a normal structure. Because the method of the present invention does not require serum, it is useful for the preparation of an artificial tissue comprising elastic fiber (for example, artificial skin, artificial blood vessels) intended to be transplanted to humans. Furthermore, because the method of the present invention does not need the use of serum, it is useful as an experimental system for identifying factors required for elastic fiber formation and regeneration. The elastic fiber regenerating agent of the present invention is useful as a reagent for cell culture, or as a cosmetic agent or a pharmaceutical.

According to the method of the present invention, it is possible to conveniently and efficiently regenerate elastic fiber retaining a normal structure. Because the method of the present invention does not require serum, it also enables preparation of an artificial tissue comprising elastic fiber (for example, artificial skin, artificial blood vessels) intended to be transplanted to humans. Because the method of the present invention does not need the use of serum, it can further be used as an experimental system for identifying the factors required for elastic fiber formation and regeneration. The elastic fiber regenerating agent of the present invention can be used as a reagent for cell culture, or as a cosmetic agent or a pharmaceutical.

This application is based on a patent application No. 2005-030864 filed in Japan (filing date: Feb. 7, 2005), the contents of which are incorporated in full herein by this reference.

---

The invention claimed is:

1. An in vitro method of promoting elastic fiber formation by a cell having the capability of regenerating elastic fiber under serum-free conditions, which method comprises:
   (a) providing a purified DANCE polypeptide;
   (b) adding an elastic fiber-formation-promoting amount of the purified DANCE polypeptide to a serum-free medium; and
   (c) culturing a cell having the capability of regenerating elastic fiber in the serum-free medium containing the purified DANCE polypeptide, thereby promoting elastic fiber formation by the cell;
   wherein the purified DANCE polypeptide is selected from the group consisting of:
   (a) a polypeptide comprising the amino acid sequence of SEQ ID NO: 1;
   (b) a polypeptide comprising the amino acid sequence of SEQ ID NO: 1 except that amino acid residues 1-23 of SEQ ID NO: 1 have been deleted, and wherein the polypeptide has elastic fiber regeneration activity;
   (c) a polypeptide comprising the amino acid sequence of SEQ ID NO: 1 except that 1 amino acid has been substituted, deleted, inserted or added, and wherein the polypeptide has elastic fiber regeneration activity;
   (d) a polypeptide comprising the amino acid sequence of SEQ ID NO: 1 except that arginine at the amino acid corresponding to position 77 of SEQ ID NO: 1 has been replaced with alanine, and wherein the polypeptide has elastic fiber regeneration activity; and
   (e) the polypeptide of (c) or (d) except that a signal sequence corresponding to amino acids residues 1-23 of SEQ ID NO: 1 has been deleted, and wherein the polypeptide has elastic fiber regeneration activity.

2. The method of claim 1, wherein theup rified DANCE polypeptide is purified human DANCE polypeptide and the cell having the capability of regenerating elastic fiber is derived from a human.

3. The method of claim 1, wherein the cell having the capability of regenerating elastic fiber is a fibroblast.

4. The method of claim 1, wherein the purified DANCE polypeptide is a polypeptide comprising the amino acid sequence of SEQ ID NO: 1.

5. The method of claim 1, wherein the purified DANCE polypeptide is a polypeptide comprising the amino acid sequence of SEQ ID NO: 1 except that amino acid residues 1-23 of SEQ ID NO: 1 have been deleted, and wherein the polypeptide has elastic fiber regeneration activity.

6. The method of claim 1, wherein the purified DANCE polypeptide is a polypeptide comprising the amino acid sequence of SEQ ID NO: 1 except that 1 amino acid has been substituted, deleted, inserted or added, and wherein the polypeptide has elastic fiber regeneration activity.

7. The method of claim 1, wherein the purified DANCE polypeptide is a polypeptide comprising the amino acid sequence of SEQ ID NO: 1 except that arginine at the amino acid corresponding to position 77 of SEQ ID NO: 1 has been replaced with alanine, and wherein the polypeptide has elastic fiber regeneration activity.

8. The method of claim 1, wherein the purified DANCE polypeptide is selected from the group consisting of polypeptides (i) and (ii) except that a signal sequence corresponding to amino acids residues 1-23 of SEQ ID NO: 1 has been deleted, and wherein the polypeptide has elastic fiber regeneration activity:
   (i) a polypeptide comprising the amino acid sequence of SEQ ID NO: 1 except that 1 amino acid has been substituted, deleted, inserted or added, and wherein the polypeptide has elastic fiber regeneration activity; and
   (ii) a polypeptide comprising the amino acid sequence of SEQ ID NO: 1 except that arginine at the amino acid corresponding to position 77 of SEQ ID NO: 1 has been replaced with alanine, and wherein the polypeptide has elastic fiber regeneration activity.

* * * * *

SEQUENCE LISTING

<160> NUMBER OF SEQ ID NOS: 1

<210> SEQ ID NO 1
<211> LENGTH: 448
<212> TYPE: PRT
<213> ORGANISM: Homo sapiens

<400> SEQUENCE: 1

```
Met Pro Gly Ile Lys Arg Ile Leu Thr Val Thr Ile Leu Ala Leu Cys
1               5                   10                  15

Leu Pro Ser Pro Gly Asn Ala Gln Ala Gln Cys Thr Asn Gly Phe Asp
            20                  25                  30

Leu Asp Arg Gln Ser Gly Gln Cys Leu Asp Ile Asp Glu Cys Arg Thr
        35                  40                  45

Ile Pro Glu Ala Cys Arg Gly Asp Met Met Cys Val Asn Gln Asn Gly
    50                  55                  60

Gly Tyr Leu Cys Ile Pro Arg Thr Asn Pro Val Tyr Arg Gly Pro Tyr
65                  70                  75                  80

Ser Asn Pro Tyr Ser Thr Pro Tyr Ser Gly Pro Tyr Pro Ala Ala Ala
                85                  90                  95

Pro Pro Leu Ser Ala Pro Asn Tyr Pro Thr Ile Ser Arg Pro Leu Ile
            100                 105                 110

Cys Arg Phe Gly Tyr Gln Met Asp Glu Ser Asn Gln Cys Val Asp Val
        115                 120                 125

Asp Glu Cys Ala Thr Asp Ser His Gln Cys Asn Pro Thr Gln Ile Cys
    130                 135                 140

Ile Asn Thr Glu Gly Gly Tyr Thr Cys Ser Cys Thr Asp Gly Tyr Trp
145                 150                 155                 160

Leu Leu Glu Gly Gln Cys Leu Asp Ile Asp Glu Cys Arg Tyr Gly Tyr
                165                 170                 175

Cys Gln Gln Leu Cys Ala Asn Val Pro Gly Ser Tyr Ser Cys Thr Cys
            180                 185                 190

Asn Pro Gly Phe Thr Leu Asn Glu Asp Gly Arg Ser Cys Gln Asp Val
        195                 200                 205

Asn Glu Cys Ala Thr Glu Asn Pro Cys Val Gln Thr Cys Val Asn Thr
    210                 215                 220

Tyr Gly Ser Phe Ile Cys Arg Cys Asp Pro Gly Tyr Glu Leu Glu Glu
225                 230                 235                 240

Asp Gly Val His Cys Ser Asp Met Asp Glu Cys Ser Phe Ser Glu Phe
                245                 250                 255

Leu Cys Gln His Glu Cys Val Asn Gln Pro Gly Thr Tyr Phe Cys Ser
            260                 265                 270

Cys Pro Pro Gly Tyr Ile Leu Leu Asp Asp Asn Arg Ser Cys Gln Asp
        275                 280                 285

Ile Asn Glu Cys Glu His Arg Asn His Thr Cys Asn Leu Gln Gln Thr
    290                 295                 300

Cys Tyr Asn Leu Gln Gly Gly Phe Lys Cys Ile Asp Pro Ile Arg Cys
305                 310                 315                 320

Glu Glu Pro Tyr Leu Arg Ile Ser Asp Asn Arg Cys Met Cys Pro Ala
                325                 330                 335
```

-continued

```
Glu Asn Pro Gly Cys Arg Asp Gln Pro Phe Thr Ile Leu Tyr Arg Asp
            340                 345                 350

Met Asp Val Val Ser Gly Arg Ser Val Pro Ala Asp Ile Phe Gln Met
        355                 360                 365

Gln Ala Thr Thr Arg Tyr Pro Gly Ala Tyr Tyr Ile Phe Gln Ile Lys
    370                 375                 380

Ser Gly Asn Glu Gly Arg Glu Phe Tyr Met Arg Gln Thr Gly Pro Ile
385                 390                 395                 400

Ser Ala Thr Leu Val Met Thr Arg Pro Ile Lys Gly Pro Arg Glu Ile
            405                 410                 415

Gln Leu Asp Leu Glu Met Ile Thr Val Asn Thr Val Ile Asn Phe Arg
            420                 425                 430

Gly Ser Ser Val Ile Arg Leu Arg Ile Tyr Val Ser Gln Tyr Pro Phe
            435                 440                 445
```